United States Patent
Nölle et al.

(10) Patent No.: US 8,848,987 B2
(45) Date of Patent: Sep. 30, 2014

(54) METHOD AND APPARATUS FOR GENERATING AN IMAGE INCLUDING EDITING COMMENTS IN A STERILE WORKING AREA OF A MEDICAL FACILITY

(75) Inventors: Martin Nölle, Radolfzell (DE);
Hans-Uwe Hilzinger, Tuttlingen (DE);
Heinz-Werner Stiller, Beringen (CH)

(73) Assignee: Karl Storz GmbH & Co. KG (DE)

( * ) Notice: Subject to any disclaimer, the term of this patent is extended or adjusted under 35 U.S.C. 154(b) by 648 days.

(21) Appl. No.: 11/405,235

(22) Filed: Apr. 17, 2006

(65) Prior Publication Data
US 2006/0257008 A1  Nov. 16, 2006

Related U.S. Application Data

(63) Continuation of application No. PCT/EP2004/011195, filed on Oct. 7, 2004.

(30) Foreign Application Priority Data

Oct. 17, 2003 (DE) .................................. 103 49 649

(51) Int. Cl.
*G06K 9/00* (2006.01)
*A61B 5/00* (2006.01)
*A61B 19/00* (2006.01)

(52) U.S. Cl.
CPC ................ *A61B 19/52* (2013.01); *A61B 19/38* (2013.01); *A61B 19/5225* (2013.01); *A61B 2019/5227* (2013.01); *A61B 5/0013* (2013.01)
USPC ........................................................ 382/128

(58) Field of Classification Search
USPC .................... 341/22, 34; 382/133, 128, 131; 600/102, 407, 101, 466; 706/23
See application file for complete search history.

(56) References Cited

U.S. PATENT DOCUMENTS 3,772,514 A  * 11/1973  Sunderland .................... 250/551
4,877,016 A    10/1989  Kantor et al. ................... 128/63
4,989,253 A  *  1/1991  Liang et al. .................... 381/110

(Continued)

FOREIGN PATENT DOCUMENTS

DE     195 34 312 A1    3/1997
DE     198 58 421 A1    6/2000

OTHER PUBLICATIONS

International Search Report, Feb. 1, 2005, 2 pages.

(Continued)

*Primary Examiner* — Nancy Bitar
(74) *Attorney, Agent, or Firm* — St. Onge Steward Johnston & Reens LLC

(57) ABSTRACT

An image that includes editing comments is generated on a medical display unit which is arranged in a sterile working area of a medical facility. An input device for generating input data representing the editing comments is also arranged in the sterile working area. First, the display unit displays a primary image, such as an endoscopic photograph from inside of a patient's body. A physician can generate the input data using the input device. Both the primary image and the input data are transmitted to an image processing unit arranged outside the sterile area. The image processing unit combines the input data and the primary image to form a secondary image including the editing comments. The secondary image is subsequently retransmitted to the display unit.

22 Claims, 1 Drawing Sheet

(56) References Cited

U.S. PATENT DOCUMENTS

| | | | |
|---|---|---|---|
| 5,257,998 A * | 11/1993 | Ota et al. | 606/130 |
| 5,788,688 A * | 8/1998 | Bauer et al. | 606/1 |
| 5,970,980 A | 10/1999 | Adair | 128/849 |
| 6,078,681 A * | 6/2000 | Silver | 382/133 |
| 6,241,672 B1 * | 6/2001 | Hochman et al. | 600/431 |
| 6,434,329 B1 * | 8/2002 | Dube et al. | 396/14 |
| 6,591,239 B1 * | 7/2003 | McCall et al. | 704/275 |
| 6,621,917 B1 * | 9/2003 | Vilser | 382/128 |
| 6,639,789 B2 * | 10/2003 | Beger | 361/681 |
| 6,791,601 B1 * | 9/2004 | Chang et al. | 348/65 |
| 7,358,987 B2 * | 4/2008 | Takeshige et al. | 348/74 |
| 2005/0272971 A1 * | 12/2005 | Ohnishi et al. | 600/101 |
| 2006/0242096 A1 * | 10/2006 | Ozaki et al. | 706/23 |
| 2007/0156017 A1 * | 7/2007 | Lamprecht et al. | 600/102 |
| 2007/0269017 A1 * | 11/2007 | Umeki et al. | 378/165 |
| 2009/0131746 A1 * | 5/2009 | Seo et al. | 600/101 |

OTHER PUBLICATIONS

Boeckeler Instruments, Inc.; Pointmaker PVI-44 Compact Video Marker; Tucson, Arizona; 1994-2002; 2 pages.

* cited by examiner

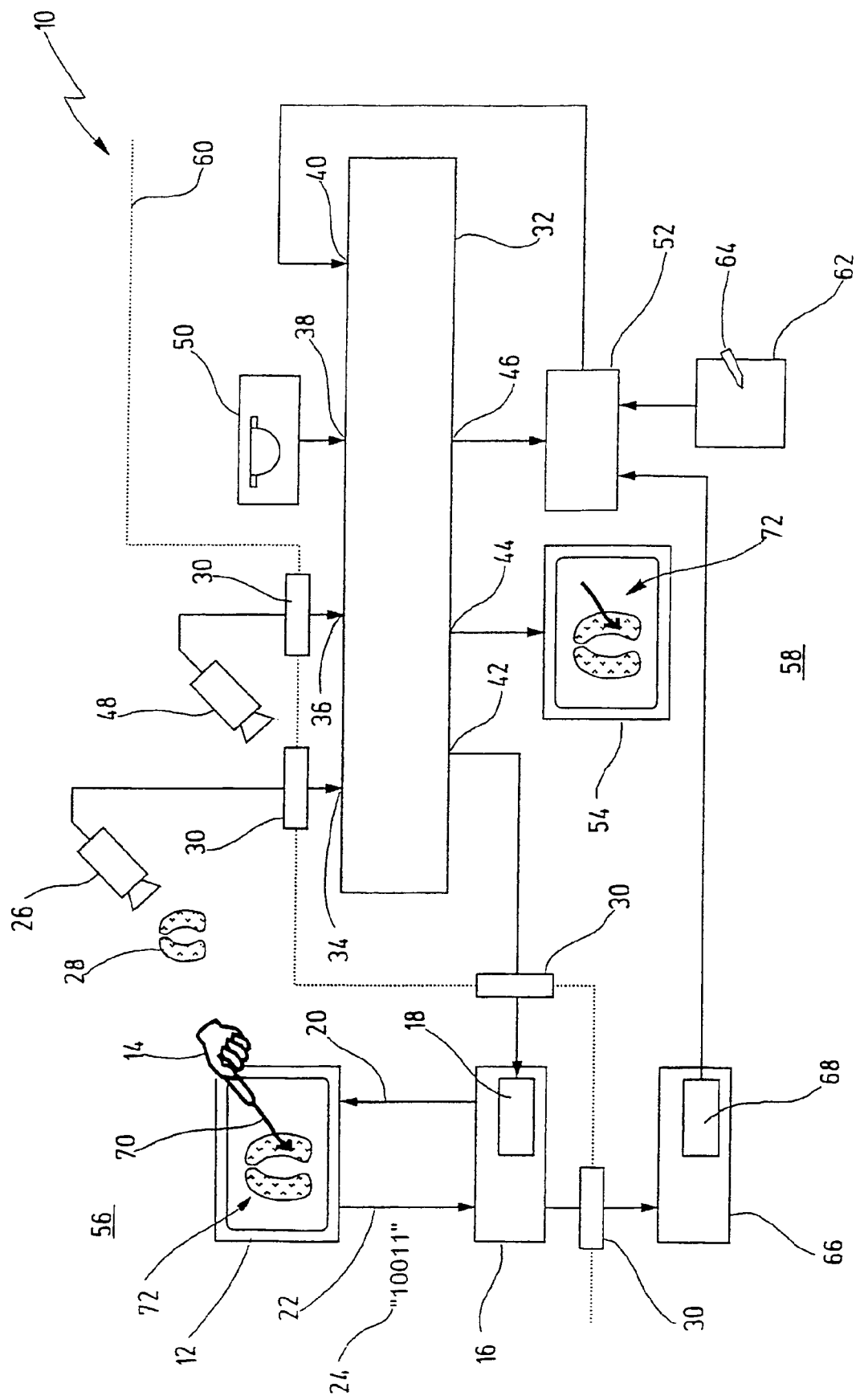

METHOD AND APPARATUS FOR GENERATING AN IMAGE INCLUDING EDITING COMMENTS IN A STERILE WORKING AREA OF A MEDICAL FACILITY

CROSS-REFERENCE TO RELATED APPLICATIONS

The present application is a continuation of international patent application PCT/EP2004/011195 filed on Oct. 7, 2004 and published as WO 2005/037093 A1 in German language, which international application claims Convention priority from German patent application DE 103 49 649.1 filed on Oct. 17, 2003.

BACKGROUND OF THE INVENTION

The present invention relates to a method and an apparatus for generating an image including editing comments in a sterile working area of a medical facility.

In modern medicine, treatments are being carried out more and more using technical imaging methods. By way of example, miniaturized cameras are inserted into the body of a patient, and the image taken by the camera is displayed to the physician on a monitor installed in his/her working area. In this way, the physician can, for example, examine an internal organ or a joint for diagnostic purposes and he/she can also carry out surgical operations in a minimally invasive fashion. In order to render the treatment of a patient as efficient and simple as possible, it is advantageous in this case when the monitor is arranged in the working area of the physician, i.e. in the sterile area. This allows the physician to track all the operations that he or she undertakes on the patient live on the monitor, the corresponding monitor image being picked up, for example, with an endoscopic camera. However, the invention is not restricted to applications in which images are generated by means of endoscopic cameras. Although this is a preferred application, the provenance of the images plays a subordinate role. For example, the images can also be X-ray images or photographs from an archive that are displayed on the monitor in the doctor's working area for the purpose of comparison, for example.

U.S. Pat. No. 5,788,688 discloses an integrated operating and control system for surgical operations on a patient, where use is made of such possibilities including the use of imaging methods.

In order to further improve the possibilities of such a system, it is desirable to provide the displayed image with commentaries, notes, marks and the like, which is generally referred to as editing comments in the following. This facilitates, for example, a discussion between a plurality of physicians in the compilation of a finding. Moreover, it is desirable for the purposes of education and training when, for example, an experienced physician can mark areas in the displayed image and provide them with commentaries.

Devices that permit an image displayed on a display unit (monitor, beamer or the like) to be provided with commentaries and marks exist for applications outside the medical field, such as for office applications and other commercial purposes. For example, Boeckeler Instruments, Inc. of Tucson, Ariz., USA, markets suitable devices under the brand name "Pointmaker®". However, these devices have the disadvantage that they are neither conceived nor approved for applications in the field of medicine and therefore cannot be used in the sterile working area.

One possibility could be the use of the commercially available devices outside the sterile working area, wherein the relevant image from the sterile working area would then additionally have to be transmitted to a second monitor arranged outside the sterile area. It is disadvantageous here that the treating physician needs to leave the sterile working area in order to insert editing comments into the displayed image.

Another possibility could be to re-equip commercially available devices so that they fulfil the requirements for use in the sterile working area of an operating room. As a further alternative, it appears feasible to develop a device suitable for medical applications that already includes the desired functionality such as is known from commercially available devices. However, both approaches are complicated and expensive.

SUMMARY OF THE INVENTION

Against this background, it is an object of the present invention to provide a method and an apparatus for generating images including editing comments in a sterile working area of a medical facility.

It is another object of the invention to provide such a method and apparatus in a simple and cost effective way.

It is yet another object of the invention to enable a physician to edit a medical image, such as an endoscopic video image, from the sterile area.

In accordance with one aspect of the invention, there is provided a method comprising the steps of: arranging a medical display unit for displaying an image in the sterile working area, arranging an input device for generating input data in the sterile working area, the input data representing the editing comments, arranging an image processing unit outside the sterile area, displaying a primary image on the display unit, reading in the input data and transmitting the input data to the image processing unit, transmitting the primary image to the image processing unit, generating a secondary image in the image processing unit by combining the primary image and the input data, and transmitting the secondary image to the display unit, and displaying the secondary image including the editing comments on the display unit.

In accordance with another aspect of the invention, there is provided an apparatus comprising a medical display unit arranged in the sterile working area for displaying a primary image, an input device arranged in the sterile working area for generating input data, the input data representing the editing comments, and an image processing unit arranged outside the sterile area, wherein the image processing unit is configured to pick up the input data and the primary image and combine them to form a secondary image, wherein the medical display unit and the image processing unit are connected via an interface such that the secondary image can be transmitted to the display unit and displayed there.

Thus, the proposed method and apparatus are based on the idea of transmitting both the primary image, to be provided with the editing comments, and the input data, which represent the editing comments, from the sterile area "to the outside world", i.e. into a non-sterile area. There, the primary image and the input data can be combined in a simple and cost effective way, where advantageous use can be made of a commercially available image processing unit for this partial step, so that the image processing unit per se does not need to be approved for medical applications. Instead of equipping a commercially available image processing unit for an application in medical fields, the processing of the image and the editing comments is thus transferred to a non-critical area in accordance with this approach. The "transferral" is performed such that a treating physician can still generate the input data from his/her sterile working area. The proposed approach therefore conjoins the advantages of the abovementioned alternative solutions.

The approach proposed here has the downside that both the input data and the primary image have to be transmitted to the image processing unit that is arranged at a distance, and this results in a considerable outlay on communication. However, it has surprisingly turned out that this outlay can be managed more easily and cost effectively than it was first possible to suppose.

Moreover, the novel method and apparatus have the advantage that the secondary image including the editing comments is directly available for further processing outside the sterile area. This further processing can include, for example, displaying on a remote training monitor and/or archiving in an electronic patient card file. The novel system therefore offers an extended field of application.

In a preferred refinement of the invention, the primary image is a medical photograph or camera picture of a patient, in particular a photograph taken endoscopically in the sterile working area.

The advantages of the invention are clearly visible in this preferred embodiment. The analysis of a medical photograph of a patient and, in particular, analysis of a current photograph of the patient during a treatment, is a case of application that becomes simpler and clearer by the new provision of editing comments. In this preferred refinement, for example, it is easier to avoid misunderstandings during a difficult operation in which a number of physicians are participating.

In a further refinement, the input device is a touch-sensitive screen that preferably also forms the display unit.

Touch-sensitive screens (also called touch screens) are known per se and are even used as display and operating units in medical facilities. In the preferred refinement, a touch-sensitive screen has the particular advantage that the treating physician can generate editing comments very easily and quickly simply by means of his/her hands. Moreover, a touch-sensitive screen is very well suited as input device for the sterile working area and, moreover, it does not require additional space due to the preferred refinement. In the preferred refinement, the input data are, in particular, the coordinates on the touch-sensitive screen at which a touch by the treating physician is detected.

In a further refinement, the input data are transmitted to the image processing unit via a DC isolation point.

This refinement has the advantage that the sterile working area and the devices used therein are partitioned off very reliably from the non-sterile outer area. The safety and reliability of the functioning of the entire apparatus is thereby increased.

In a further refinement, the input data are subjected to protocol conversion during transmission to the image processing unit. Consequently, in a preferred refinement of the novel apparatus, there is provided a protocol converter that, preferably, is designed in the form of an interface module, in particular an interface card.

This refinement has the advantage that it is possible to use any desired image processing unit, which can even be interchangeable, simply by adapting the protocol converter. In particular, use of commercially available image processing units is thereby facilitated, and this permits a particularly cost-effective implementation.

In a further refinement, the input data are transmitted to the image processing unit in a digital format. Moreover, it is preferred when the primary image is transmitted to the image processing unit as an analog image signal.

In principle, the input data could also be transmitted to the image processing unit in analog form, or the primary image could be transmitted in digital form. However, by contrast, the preferred refinements facilitate the practical implementation. In the case of digital input data, it is possible to implement protocol conversion relatively easily and cost effectively by software. By contrast, using present day means the primary image can be transmitted more simply and quickly as an analog image signal rather than in digital form. Moreover, components that are cost-effective and tried and tested can be used in this case.

In a further refinement, the secondary image is displayed on a second display unit that is arranged outside the sterile working area.

This refinement utilizes the possibilities of the novel method in a very advantageous way, since education and training, data archiving and also video conferences, in which experts sitting far away from one another participate, are substantially simplified.

It goes without saying that the features mentioned above and those yet to be explained below can be used not only in the combination respectively specified, but also in other combinations or on their own without departing from the scope of the present invention.

BRIEF DESCRIPTION OF THE DRAWINGS

In the sole FIGURE, a preferred exemplary embodiment of the invention is illustrated in a simplified block diagram.

DETAILED DESCRIPTION OF THE INVENTION

A medical facility is denoted in its entirety by the reference numeral 10 in the FIGURE. The facility 10 includes a display unit 12 which is a touch-sensitive screen in the preferred exemplary embodiment. However, as an alternative to this, the display unit 12 could also be an analog tube monitor, a simple LCD monitor, a beamer or any other display unit. In the preferred exemplary embodiment, the touch-sensitive screen 12 simultaneously forms an input device, and this is indicated here by a hand 14 of an operator.

Reference numeral 16 denotes a PC (personal computer) that is designed for medical purposes and is equipped with what is called a framegrabber card 18. The task of the framegrabber card 18 is to pick up an analog video signal, in particular a so-called S-VHS signal, to digitize it and subsequently make it available to the internal processing unit (not illustrated here) of the PC.

The PC 16 is connected to the touch-sensitive screen 12 via two connections 20, 22. Connection 20 is a conventional video signal connection, such as a VGA connection or a DVI connection, via which the display unit is connected to the PC. Consequently, the PC 16 drives the display unit 12 via the connection 20.

In the preferred embodiment, connection 22 is a digital data connection via which input data 24 are transmitted from the touch-sensitive screen 12 to the PC 16. Here, the connection 22 is a serial RS-232 connection, in particular. However, it could also be, for example, a PS2 connection, a USB connection or a parallel data connection. The PC 16 evaluates the input data 24 as if they were input data from a mouse.

A camera unit, which here includes, in particular, an endoscopic camera and an appropriate control device (not illustrated separately), is denoted by reference numeral 26. The camera unit 26 is used, for example, to record an internal organ 28 of a patient (not illustrated here). The camera unit 26 is connected to what is called a video crossbar, via an isolation amplifier 30 or an isolating transformer. As an alternative to the block diagram illustration shown here, the isolation amplifier 30 could, for example, also be integrated in the camera unit 26 or in the abovementioned control unit.

The video crossbar 32 has a plurality of inputs 34, 36, 38, 40 to which a video signal source can be connected in each case. Moreover, the video crossbar 32 has a row of outputs 42, 44, 46 at which video signals are output. In the exemplary embodiment shown, both the signals at the video inputs 34-40 and the video signals at the outputs 42-46 are S-VHS signals. However, other types of video signals could also be used here.

The camera unit 26 is connected to the input 34 of the video crossbar 32 via the isolation amplifier 30. A further camera unit 48 is connected to the input 36 via a further isolation amplifier. In contrast to camera unit 26, camera unit 48 is here, for example, a 3D camera with an appropriate control unit that permits recording of 3-dimensional images. Moreover, other types of video signal sources could also be connected here.

By way of example, for another video source, reference numeral 50 is used to denote a CD player or DVD player that is connected to the input 38 of the video crossbar 32. The CD player or DVD player 50 serves the purpose, for example, of providing archived image material for outputting on the display unit 12.

An image processing unit 52 is connected to the input 40 of the video crossbar 32. The image processing unit 52 is preferably a commercially available image processing unit for superimposing handwritten editing comments on a video image. Here, it is preferably a unit that is marketed by Boeckeler Instruments, Inc., 4650 South Butterfield Drive, Tucson, Ariz., USA under the brand name "Pointmaker®" PVI-44.

Furthermore, the image processing unit 52 is also connected to the output 46 of the video crossbar 32 such that a loop is formed. Here, a second display unit 54 is connected to the output 44 of the video crossbar 32. The output 42 is connected to the framegrabber card 18 via a further isolation amplifier 30. It goes without saying that the configuration shown is exemplary and, in particular, that the second camera unit 48, the CD/DVD player 50 and the second display unit 54 are not required to implement the invention. Moreover, use of the video crossbar 32 is only a preferred exemplary embodiment, too. In particular, it is the task of the video crossbar 32 to switch the video signals present at the various inputs 34-40 to one or more of the outputs 42-46 in optional fashion. If only one video source, such as the camera unit 26, is being used, it is sufficient for the video signal thereof to be fed to the framegrabber card 18 and the image processing unit 52 via a splitter (not illustrated here). However, in this case as well, it is preferred to use the isolation amplifiers 30 in order to ensure DC isolation between the sterile working area (denoted here by reference numeral 56) and the non-sterile area 58.

The isolation between the sterile area 56 and the non-sterile area 58 is indicated symbolically by a line 60.

Furthermore, reference numeral 62 denotes a digitizer tablet which enables manual inputs by means of a stylus 64, wherein the inputs are read in by the image processing unit 52 for further processing. Consequently, the digitizer tablet 62 is connected here to the image processing unit 52 via an appropriate connection. Again, the digitizer tablet 62 is not mandatory for the practical implementation of the invention, and it is therefore optional.

Moreover, reference numeral 66 denotes an interface unit that is equipped in the present exemplary embodiment with an interface module 68 in the form of a plug-in card (printed circuit board). The interface unit 66 is connected on the output side via the interface module 68 to a further input of the image processing unit 52. The interface unit 66 is connected on the input side to the PC 16 via a further isolation amplifier 30 (that could also be integrated in the interface unit 66). In a preferred exemplary embodiment, the connection between the PC 16 and the interface unit 66 is a digital bus connection, in particular a CAN-based bus connection, such as is specifically marketed by the applicant of the present invention under the brand name SCB for networking medical facilities. The connection between the interface module 68 and the image processing unit 52 is an RS-232 connection in the preferred exemplary embodiment. Alternatively, however, it could also be a USB connection, a parallel data connection or any other kind of data connection, which is preferably standardized. The interface module 68 carries out a protocol conversion by converting input data 24 (in the data format of the SCB connection in the preferred exemplary embodiment) received from the PC 16 into the digital data format of the RS-232 connection to the image processing unit 52.

The apparatus 10 operates as follows: The camera unit 26 is used to record the patient's organ 28. The video signal of the camera unit 26 is fed via the video crossbar 32 to the framegrabber card 18, digitized by the latter and subsequently output on the touch-sensitive screen 12 via the PC 16. This output image is the primary image in terms of the present invention.

The treating physician now has the possibility of using his hand 14 to mark areas on the touch-sensitive screen. The appropriate coordinates are transmitted to the PC 16 as input data 24 and detected there as mouse movements. The treating physician can use the input data to control, inter alia, medical facilities (not illustrated here) connected to the PC 16, such as insufflators, an operating table or the operational lighting, for example. Furthermore, by means of an appropriate input command, he can put the PC 16 into a "marking or character mode" in which subsequent inputs on the touch-sensitive screen 12 are interpreted as editing comments. The PC 16 converts the mouse movements then detected into graphic symbols. For example, a graphic symbol in the form of a marking arrow drawn by hand is denoted in the FIGURE by reference numeral 70. However, symbol 70 is not displayed directly on the display unit 12. Rather, the PC 16 transmits the mouse coordinates to the interface unit 66 where they are converted by means of the interface module 68 into the data format of the image processing unit 52. Furthermore, the image processing unit 52 receives the primary image via the output 46 of the video crossbar 32 and superimposes the symbol 70 on said image. Subsequently, the image processing unit 52 transmits the combined image to the video crossbar 32 (input 40) as secondary image. From there, it passes via the framegrabber card 18 to the display unit 12 on which the secondary image 72 provided with the symbol 70 is now displayed. The treating physician can then insert further marks or comments that are once again displayed in the same way on the display unit 12, the image initially displayed on the display unit 12 in each case being the primary image in the meaning of the present invention.

In the exemplary embodiment shown here, the secondary image 72 is also displayed on the spatially remote display unit 54 that is available, for example for training purposes or else for data archiving.

What is claimed is:

1. A method for generating an image including editing comments in a sterile working area of a medical facility, the method comprising the steps of:
   arranging a medical display unit for displaying an image in the sterile working area, arranging an input device for generating input data in the sterile working area, the input data representing the editing comments, arranging an image processing unit outside the sterile area, providing an endoscopic camera for taking a primary image, displaying the primary image on the display unit, reading in the input data and transmitting the input data to the image processing unit via at least one isolation amplifier to ensure DC isolation between the sterile working area and outside the sterile working area, providing a video crossbar connected to the endoscopic camera via the at least one isolation amplifier, transmitting the primary image to the image processing unit, generating a secondary image in the image processing unit by combining the primary image and the input data outside the sterile area, and transmitting the secondary image to the display unit, and displaying the secondary image including the editing comments on the display unit.

2. The method of claim 1, wherein the primary image is a camera picture of a patient taken endo-scopically in the sterile working area.

3. The method of claim 1, wherein the input device is a touch-sensitive screen.

4. The method of claim 3, wherein the touch-sensitive screen also forms the display unit.

5. The method of claim 1, wherein the input data are transmitted to the image processing unit via a DC isolation point.

6. The method of claim 1, wherein the input data are subjected to protocol conversion during transmission to the image processing unit.

7. The method of claim 1, wherein the input data are transmitted to the image processing unit in a digital format.

8. The method of claim 1, wherein the primary image is transmitted to the image processing unit as an analog image signal.

9. The method of claim 1, further comprising the step of arranging a second display unit outside the sterile working area, wherein the secondary image is also displayed on the second display unit.

10. An apparatus for generating an image including editing comments in a sterile working area of a medical facility, the apparatus comprising:
 a medical display unit arranged in the sterile working area for displaying a primary image,
 an input device arranged in the sterile working area for generating input data, the input data representing the editing comments, and
 an image processing unit arranged outside the sterile area, wherein the image processing unit is configured to pick up the input data and the primary image and combine them to form a secondary image outside the sterile area,
 an endoscopic camera for taking the primary image,
 a video crossbar connected to the endoscopic camera via at least one isolation amplifier,
 wherein the medical display unit and the image processing unit are connected via an interface and at least one isolation amplifier to ensure DC isolation between the sterile working area and outside the sterile working area, such that the secondary image can be transmitted to the display unit and displayed there.

11. The apparatus of claim 10, wherein the input device is a touch-sensitive screen.

12. The apparatus of claim 11, wherein the touch-sensitive screen also forms the display unit.

13. The apparatus of claim 10, further comprising a protocol converter arranged between the input device and the image processing unit, the protocol converter being configured to effect a protocol conversion on the input data during transmission to the image processing unit.

14. The apparatus of claim 10, wherein the input data are transmitted to the image processing unit in a digital format.

15. The apparatus of claim 10, wherein the primary image is transmitted to the image processing unit as an analog image signal.

16. The apparatus of claim 10, further comprising a second display unit arranged outside the sterile working area, the second display unit also being configured to display the secondary image.

17. An apparatus for generating an image including editing comments in a sterile working area of a medical facility, the apparatus comprising:
 a medical display unit arranged in the sterile working area for displaying a primary image,
 an input device arranged in the sterile working area for generating input data, the input data representing the editing comments, and
 an image processing unit arranged outside the sterile area, wherein the input data is transmitted to the image processing unit via a DC isolation point,
 an endoscopic camera for taking the primary image,
 a video crossbar connected to the endoscopic camera via at least one isolation amplifier,
 wherein the image processing unit is configured to pick up the input data and the primary image and combine them to form a secondary image outside the sterile area,
 wherein the medical display unit and the image processing unit are connected via an interface and at least one isolation amplifier to ensure DC isolation between the sterile working area and outside the sterile working area, such that the secondary image can be transmitted to the display unit and displayed there.

18. The apparatus of claim 17, further comprising a protocol converter arranged between the input device and the image processing unit, the protocol converter being configured to effect a protocol conversion on the input data during transmission to the image processing unit.

19. The apparatus of claim 17, wherein the input data are transmitted to the image processing unit in a digital format.

20. The apparatus of claim 10, wherein the video crossbar has a plurality of inputs and a row of outputs.

21. The apparatus of claim 20, wherein the signals at the plurality of inputs and the row of outputs are S-VHS signals.

22. The apparatus of claim 10, wherein the isolation amplifier is integrated in the endoscopic camera.

* * * * *